(12) United States Patent
Cabrerizo et al.

(10) Patent No.: US 10,195,456 B2
(45) Date of Patent: Feb. 5, 2019

(54) LOW INTENSITY MAGNETIC FIELD DEVICE FOR COSMETIC SKIN TREATMENT

(71) Applicants: Mercedes Cabrerizo, Miami, FL (US); Malek Adjouadi, Miami, FL (US); Niovi Rojas, Miami, FL (US); Juan Perez, Miami, FL (US)

(72) Inventors: Mercedes Cabrerizo, Miami, FL (US); Malek Adjouadi, Miami, FL (US); Niovi Rojas, Miami, FL (US); Juan Perez, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 344 days.

(21) Appl. No.: 15/059,639

(22) Filed: Mar. 3, 2016

(65) Prior Publication Data

US 2017/0252574 A1    Sep. 7, 2017

(51) Int. Cl.
*A61N 2/02* (2006.01)
*A61N 2/00* (2006.01)

(52) U.S. Cl.
CPC ............. *A61N 2/02* (2013.01); *A61N 2/004* (2013.01)

(58) Field of Classification Search
CPC ............. A61N 2/00; A61N 2/02; A61N 2/004
USPC .................................................... 600/9–15
See application file for complete search history.

(56) References Cited

U.S. PATENT DOCUMENTS

| | | | | |
|---|---|---|---|---|
| 4,641,633 A | * | 2/1987 | Delgado | A61N 2/00 600/13 |
| 5,224,922 A | * | 7/1993 | Kurtz | A61N 2/02 128/898 |
| 5,429,301 A | * | 7/1995 | Franks | B65D 83/384 222/145.1 |
| 5,480,373 A | * | 1/1996 | Fischer | A61N 2/02 600/14 |
| 5,718,662 A | * | 2/1998 | Jalinous | A61N 2/006 128/897 |
| 6,155,966 A | * | 12/2000 | Parker | A61N 2/02 600/13 |
| 2008/0234534 A1 | * | 9/2008 | Mikas | A61N 2/02 600/14 |
| 2010/0081858 A1 | * | 4/2010 | Sotiriou | A61N 2/12 600/13 |
| 2011/0263925 A1 | * | 10/2011 | Bratton | A61N 2/004 600/14 |
| 2016/0030761 A1 | * | 2/2016 | Butters | A61N 2/004 600/14 |

OTHER PUBLICATIONS

Aaron, Roy K., et al. "Treatment of Nonunions with Electric and Electromagnetic Fields," 2004, *Clin Orthop RelatRes*, 419:21-29.

(Continued)

*Primary Examiner* — Samuel Gilbert
(74) *Attorney, Agent, or Firm* — Saliwanchik, Lloyd & Eisenschenk

(57) ABSTRACT

Devices and methods for cosmetic skin treatment using a magnetic field are provided. A device can include a case, a stimulation head coupled with the case and including at least one coil of conductive wire for generating a magnetic field, and an electronic circuit housed in the case for driving the coils to generate the magnetic field.

18 Claims, 7 Drawing Sheets

(56) References Cited

OTHER PUBLICATIONS

Ågren, Magnus S. et al. "Collagenase During Burn Wound Healing: Influence of a Hydrogel Dressing and Pulsed Electrical Stimulation," 1994, *Plastic and Reconstructive Surgery*, 94:518-524.

Athanasiou A. et al. "The Effect of Pulsed Electromagnetic Fields on Secondary Skin Wound Healing: An Experimental Study," 2007, *Bioelectromagnetics*, 28(5):362-368.

Bassett, C. Andrew, "Beneficial Effects of Electromagnetic Fields," 1993, J CellBiochem 51(4):387-393.

Bouzarjomehri F. et al. "Effects of Low Frequency Pulsed Electromagnetic Fields on Wound Healing in Rat Skin," 2000, *Arch Intern Med*, 3:23-27.

Howard Jeffrey D. et al. "Rapid Granulation Tissue Regeneration by Intracellular ATP Delivery—A Comparison with Regranex," 2014, *PLoSOne*, 9(3): e91787.

Macias, Melissa Y. et al. "Directed and Enhanced Neurite Growth With Pulsed Electromagnetic Field Stimulation," 2000, *Bioelectromagnetics*, 21(4):272-286.

O, Patino et al. "Pulsed Electromagnetic Fields in Experimental Cutaneous Wound Healing in Rats," 1996, *J Burn Care Rehabil*, 17:528-531, Abstract only.

Ryaby, JT "Clinical Effects of Electromagnetic and Electric Fields on Fracture Healing," 1998, *Clin Orthop Relat Res*,(355Suppl):S205-S215, Abstract only.

Strauch, Berish et al. "Pulsed Magnetic Fields Accelerate Cutaneous Wound Healing in Rats," 2007, *Plast Reconstr Surg*, 120(2):425-430.

Walker, Janet L. et al. "Enhancement of Functional Recovery Following a Crush Lesion to the Rat Sciatic Nerve by Exposure to Pulsed Electromagnetic Fields," 1994, *Experimental Neurology*, 125(2):302-305.

\* cited by examiner

LOW INTENSITY MAGNETIC FIELD DEVICE FOR COSMETIC SKIN TREATMENT

GOVERNMENT SUPPORT

This invention was made with government support under a grant (MRI-R2: Development of an Instrument for Information Science and Computing in Neuroscience—CNS: 0959985, FIU: 800000573) awarded by the National Science Foundation. The government has certain rights in the invention.

BACKGROUND

There is a great variety of literature discussing the effects of magnetic field on tissue repair, including bone formation, tendon healing, axonal regeneration, and wound healing (Bassett, 1993; Agren et al., 1994; Walker et al., 1994; Ryaby, 1998; 1999; Macias et al., 2000; Aaron et al., 2004). Additionally, skin care is a major industry, both in the United States and globally. There is always a need in the art for devices and methods to improve skin health and appearance.

BRIEF SUMMARY

The subject invention provides novel and advantageous devices and methods for cosmetic skin treatment using a magnetic field, as well as methods of fabricating and using such devices. A device can include one or more coils (e.g., micro-coils) for generating a magnetic field, such as a low intensity magnetic field. The device can be a hand-held and/or portable device and can include a stimulation head having the one or more coils. The device can be used to apply a magnetic field to a patient (e.g., a human patient) for cosmetic skin treatment.

In an embodiment, a handheld device for skin treatment can include a case, a stimulation head coupled with the case and comprising at least one coil of conductive wire for generating a magnetic field, and an electronic circuit, housed in the case, for driving the at least one coil to generate the magnetic field. The electronic circuit can be configured to drive the at least one coil to generate a main pulse of the magnetic field at a main frequency, and the main pulse can include a plurality of sub-pulses at a sub-frequency that is greater than the main frequency.

DETAILED DISCLOSURE

The subject invention provides novel and advantageous devices and methods for cosmetic skin treatment using a magnetic field, as well as methods of fabricating and using such devices. A device can include one or more coils (e.g., micro-coils) for generating a pulsed electromagnetic field (PEMFT), such as a low intensity magnetic field. The device can be a hand-held and/or portable device and can include a stimulation head having the one or more coils. The device can be used to apply a magnetic field to a patient (e.g., a human patient) for cosmetic skin treatment. The device uses inductive coupling, making it safer than conventional devices that use capacitive coupling.

The subject invention applies beneficial effects of magnetic stimulation to skin tissue through the use of low cost and user friendly devices. Devices of the subject invention can be used on a patient's (e.g., a human patient) face and/or body. The device can be used by, for example, health care providers, entities in the cosmetics industry, and consumers themselves.

Magnetic stimulation induces micro-currents and ion movement in tissue to activate and rebalance damaged cells and increment the levels of carbon dioxide, which serves as a mediator for skin repair. Current induction through magnetic stimulation can also increase adenosine triphosphate (ATP) levels, increase circulation, increase collagen production, and improve skin complexion and appearance. Other benefits include reduction in fine lines and wrinkles, improved skin tone, and increased skin elasticity. Because embodiments of the subject invention can produce frequencies in a low range, heating action is not induced, making this product safe for personal use and avoiding skin atrophy.

Figure 1:
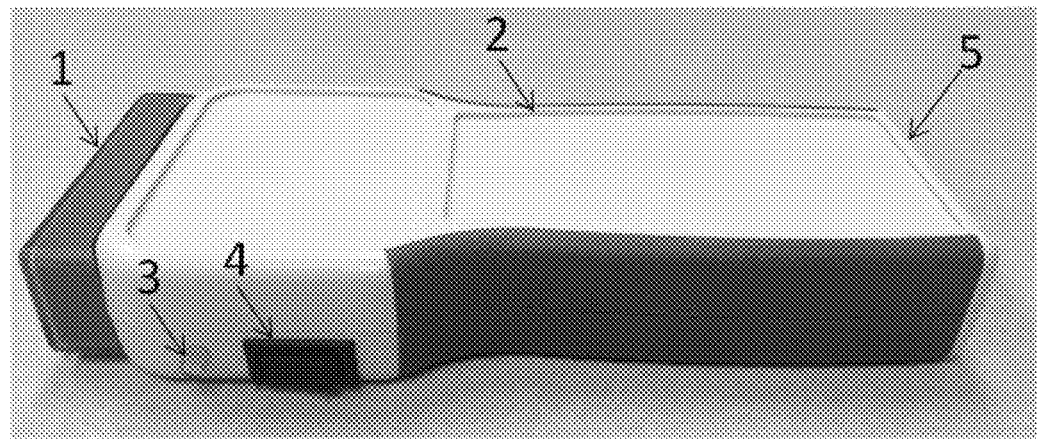
FIG. 1 is an image of a device according to an embodiment of the present invention.

FIG. 1 shows an image of a device according to an embodiment of the subject invention. Referring to FIG. 1, a device can include a stimulation head 1, which can include one or more coils (e.g., micro-coils) for providing magnetic stimulation. The stimulation head 1 can be made of any suitable materials known in the art. For example, the stimulation head 1 can be polycarbonate. The body or case 2 can be designed to be hand-held and also act as a vessel for other components of the device. For example, circuit components and/or a power source to drive the magnetic stimulation can be housed within the case 2. The case 2 can include a higher-friction material (e.g., rubber) on the sides thereof to improve grip (depicted as the dark, unlabeled portion of the case 2 in FIG. 1). The case 2 can include one or more of: a power switch 4, an indicator light 3 (e.g., an LED indicator), and a power port 5, such as a connector for charging a power source of the device from an external power source (e.g., a mini-USB connector or a power cord connector). The power port 5 can also be used for connecting a wire to an external power source that can provide power to the device during operation (e.g., an AC/DC convertor).

Figure 2:
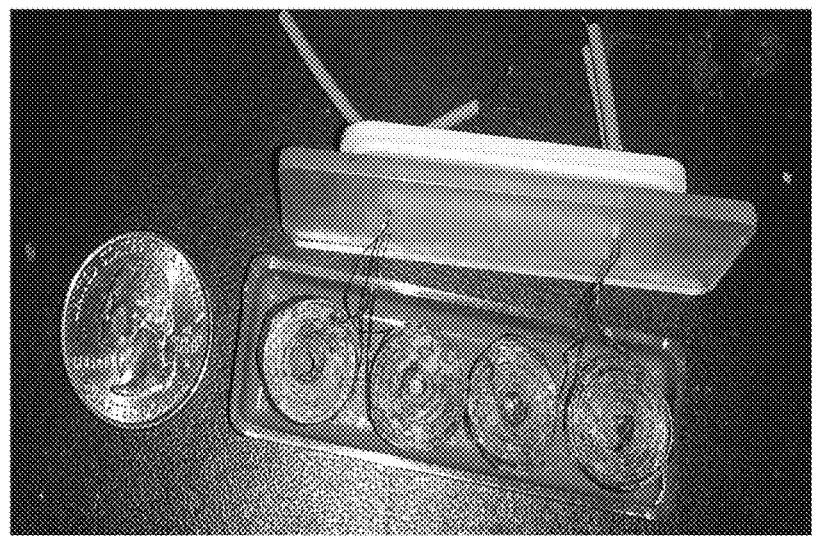
FIG. 2 is an image of an opened stimulation head of a device according to an embodiment of the subject invention.

Referring to FIG. 2, in an embodiment, the stimulation head 1 can include four coils (e.g., micro-coils). Each coil can have a diameter smaller than that of a quarter, as depicted in FIG. 2, though embodiments are not limited thereto. In one example, each of the four coils can have an outside diameter of 6 mm, an internal diameter of 4.5 mm, and consist of 500 windings of #32 (0.2032-0.254 mm) copper wire. In other embodiments, the diameters can range from 5-7 mm, 8-12 mm, 14-18 mm, 20-24 mm, or 26-30 mm.

In an embodiment, the power source of the device can be a battery, such as a rechargeable battery (e.g., a lithium ion battery). The voltage of the battery can be, for example, 9 volts (V) or about 9 V, though embodiments are not limited thereto.

The indicator light 3 can light up a particular color when stimulation pulses occur and/or when battery life is low. For example, a green LED can light up to indicate stimulation pulses are occurring and/or a red LED can light up to indicate that the battery is low (e.g., 90% or less of the battery capacity, or less than 90% of the battery capacity, such as below 8.1 V for a 9 V battery).

Figure 3:
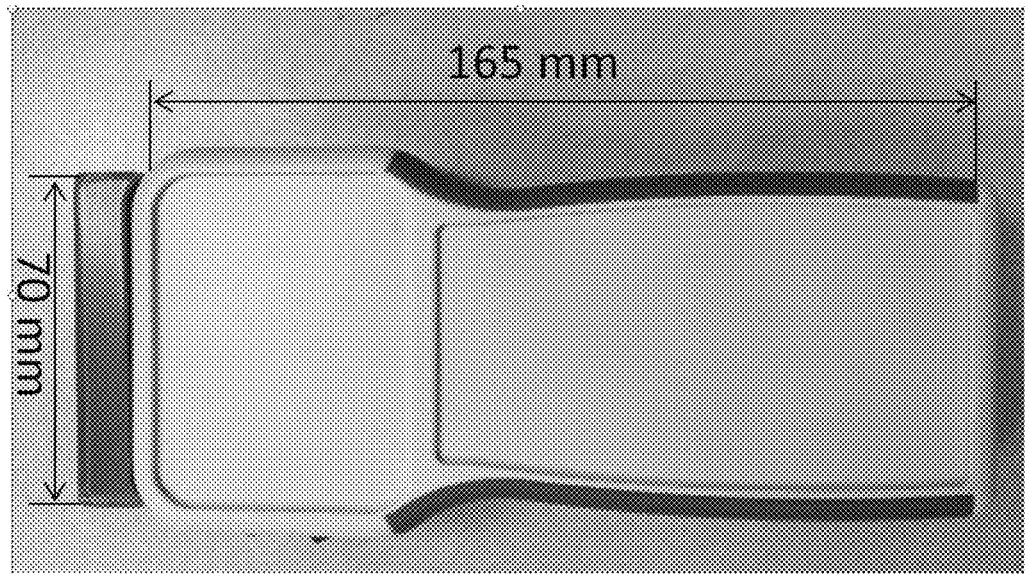
FIG. 3 is a top view of the device of FIG. 1.
Figure 4:
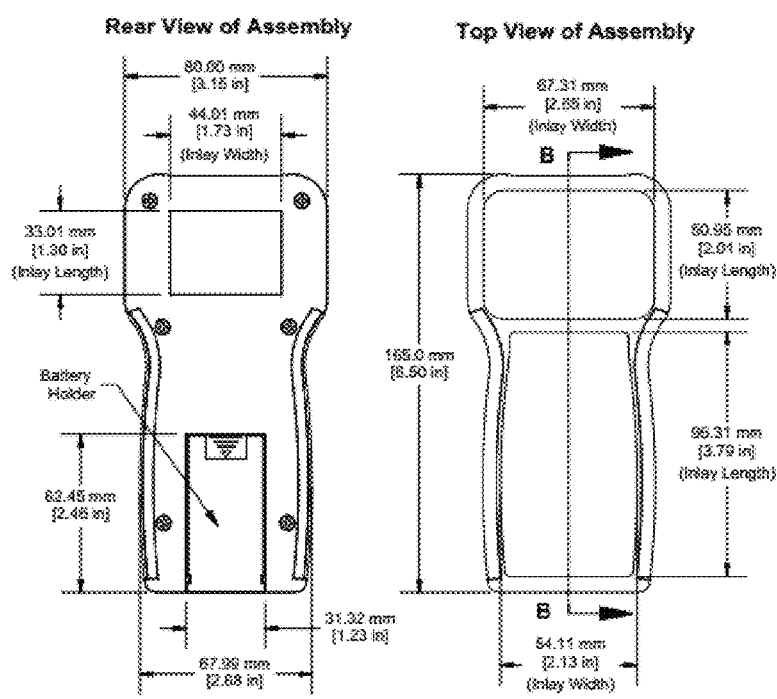
FIG. 4 is a schematic diagram of a device according to an embodiment of the subject invention.

FIG. 3 shows a top view of a device of the subject invention, and FIG. 4 shows a schematic view of the device. Referring to FIG. 3, the stimulation head can have a length of 70 mm and its width (the perpendicular direction to the length on the stimulation head applicator plane) and height (perpendicular to the applicator surface) are not shown. However, for example, the height (perpendicular to the applicator surface) of the stimulation head can range from 5 mm to 30 mm, the width of the stimulation head can range from 6 mm to 40 mm, and the length of the stimulation head can range from 25 mm to 120 mm. Though FIGS. 3 and 4 provide values for the dimensions of the device, these are for exemplary purposes only and should not be construed as limiting. Any or all of these dimensions can have a different value.

Figure 5:
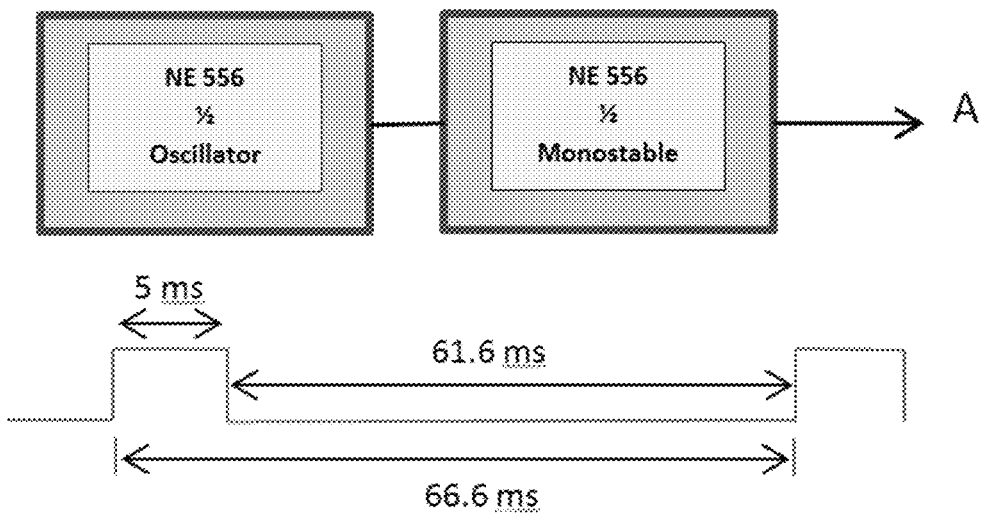
FIG. 5 is a diagram of hardware components and a waveform according to an embodiment of the subject invention.
Figure 6:
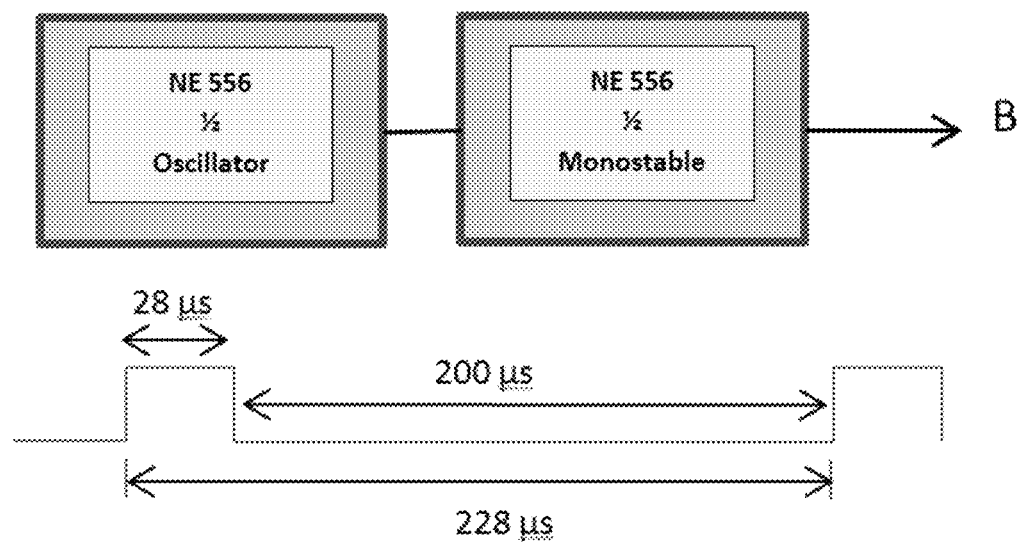
FIG. 6 is a diagram of hardware components and a waveform according to an embodiment of the subject invention.
Figure 7:
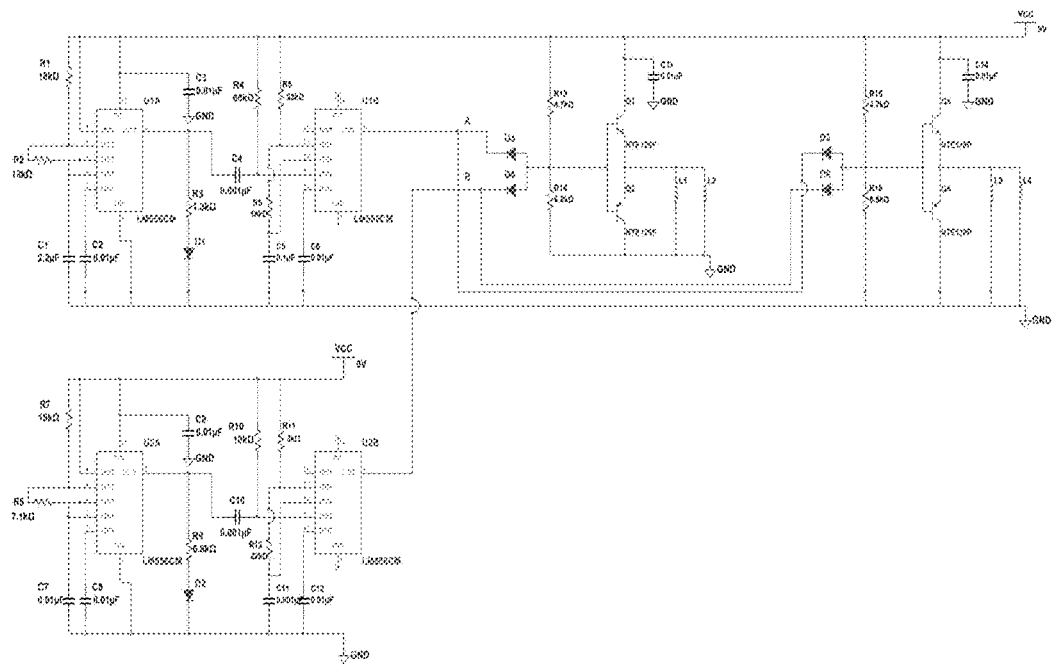
FIG. 7 is a schematic diagram of electronic circuits within a device according to an embodiment of the subject invention.

FIG. 5 shows a block diagram for hardware components (top section of FIG. 5) that can be used to drive magnetic stimulation in a device of the subject invention, as well as an example waveform that can be produced by these hardware components (bottom section of FIG. 5). FIG. 6 also shows a block diagram for hardware components (top section of FIG. 6) that can be used to drive magnetic stimulation in a device of the subject invention, as well as an example waveform that can be produced by these hardware components (bottom section of FIG. 6). FIG. 7 shows a circuit diagram with details of the hardware components of FIGS. 5 and 6. Though FIGS. 5 and 6 show values for the pulses of the waveforms and FIG. 7 shows values for the various circuit components (resistance, capacitance, etc.), these are for exemplary purposes only and should not be construed as limiting. Any or all of these components can have a different value. In addition, the circuit and hardware components for driving the magnetic stimulation can be different from what is depicted; FIGS. 5-7 are provided for exemplary purposes and to illustrate one embodiment of the subject invention.

Referring to FIG. 7, the U1A element of the integrated circuit NE556 (astable multi-vibrator) represented in FIG. 5 can generate a main frequency of stimulation, which can trigger element U1B at the beginning of each main frequency cycle. The main frequency can be, for example, 15 Hertz (Hz) (duration of 66.6 milliseconds (ms)), though embodiments are not limited thereto. The U1B element of the integrated circuit NE556 can operate as a monostable circuit, providing a main pulse having a duration of a portion of each cycle. For example, the main pulse can have a duration of 5 ms every 66.6 ms (output A coming from U1B, pin #9), with a rest period of 61.6 ms. In order to change the frequency levels, different resistors and capacitors can be applied in the circuit. Other suitable ranges for the main frequency include 10-12 Hz, 12-14 Hz, 14-16 Hz (as discussed above), 16-18 Hz, and 18-20 Hz. Other suitable ranges for the main pulse include 2.5-3.5 ms, 3.5-4.5 ms, 4.5-5.5 ms (as discussed above), 5.5-6.5 ms, 6.5-7.5 ms, and 8.5-10 ms, 12-14 ms, and 16-18 ms. Intensity can be changed as well by changing the input voltages and suitable intensity ranges at 1 mm distance from the stimulation head include 5-7 Gauss 7-9 Gauss, 9-11 Gauss, 11-13 Gauss, and 13-15 Gauss.

The second integrated circuit NE556 (U2A, U2B), as represented in FIG. 6, has similar functionality to that represented in FIG. 5 (NE556 (U1A, U1B)), but it provides a sub- or micro-frequency for a given period, within which a pulse can be provided for a portion thereof. For example, the sub-frequency can be 4.386 kHz, though embodiments are not limited thereto. Other suitable ranges for the sub-frequency include 4.0-4.1 kHz, 4.1-4.2 kHz, 4.2-4.3 kHz, 4.3-4.4 kHz (as discussed here), 4.4-4.5 kHz, 4.5-4.6 kHz, 4.6-4.7 kHz, 4.7-4.8 kHz, 4.8-4.9 kHz, and 4.9-5.0 kHz. With a frequency of 4.386 kHz, the period is 228 microseconds (μs). Within this period, a sub-pulse can be provided for, e.g., 28 μs (output B coming from U2B pin #9), with a rest period of 200 μs. However, other suitable ranges for the sub-pulse include 20-22 μs, 22-24 μs, 24-26 μs, 26-28 μs, 28-30 μs, and 30-32 μs, and 32-36 μs.

The output signals from A and B can be added through D3 and D4 and amplified using transistors Q1 and Q2, which can be configured as a complimentary pair. The output of Q1 and Q2 can then power the stimulation coils L1 and L2, which can be present within the stimulation head 1 of the device. A parallel circuit can also take output signals A and B, add them in D5 and D6, and amplify them using Q3 and Q4. This output can then be used to power stimulation coils L3 and L4, which can also be within the stimulation head 1.

Figure 9:
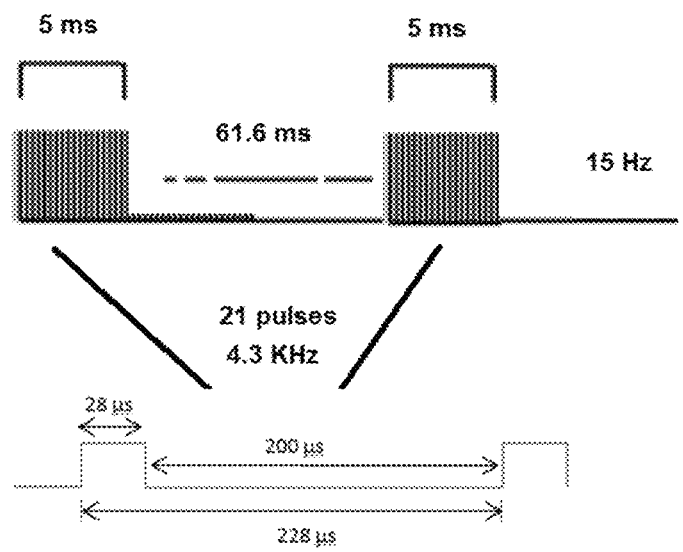
FIG. 9 illustrates a waveform produced by a device according to an embodiment of the subject invention.

In an embodiment, the main pulse can contain a set amount of sub-pulses, which can have a higher frequency than that of the main pulse. This concept is illustrated in FIG. 9, which displays time and frequency values that are for exemplary purposes only and should not be construed as limiting. Referring to FIGS. 5, 6, and 9, and the exemplary values provided therein, a 5 ms main pulse can be output every 66.6 ms. Each main pulse can include, for example, 21 sub-pulses, each having a duration of 28 μs. The sub-pulses can be repeated every 228 μs, but only during the main pulses.

The frequency of stimulation is a very important parameter for a treatment device. The stimulation from the device of the subject invention can include a main pulse having a main frequency and made up of a plurality of sub-pulses having a sub-frequency. For example, referring to the values shown in FIG. 9, the main pulse can have a frequency of 15 Hz with a pulse duration of a portion of the period (e.g., 5 ms per 66.6 ms). The sub-pulses can have a frequency of, e.g., 4.386 kHz, with a pulse duration of a portion of the period (e.g., 28 μs per 228 μs), resulting in 21 sub-pulses per main pulse. The stimulation can be applied continuously when the device is turned on, not including rest periods that may be present within the period of the main frequency and/or the sub-frequency (i.e., the 61.6 ms and 200 μs rest periods depicted in FIG. 9).

Figure 8:
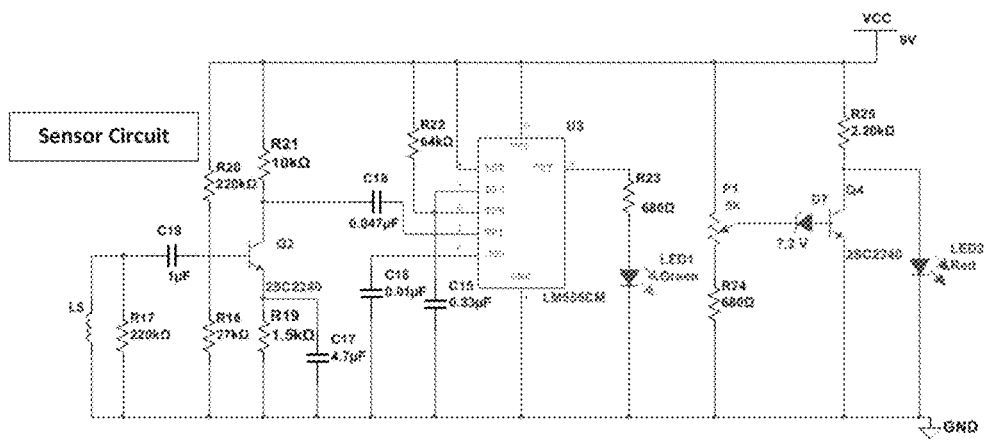
FIG. 8 is a schematic diagram of electronic circuits within a device according to an embodiment of the subject invention.

Referring to FIG. 8, the power supply (e.g., a DC power supply or a battery, such as a 9 V lithium ion rechargeable battery) can supply power to the device. The power level (e.g., the battery level) can be detected by a Zener diode D7 (e.g., 7.2V) through transistor Q4. An indicator light (e.g., a red LED, though embodiments are not limited thereto) can be activated when the power level is lower than a threshold (e.g., when the 9V battery voltage is lower than 8.1 V). At this point, the device can continue stimulation for an additional period of time (e.g., for approximately 30 minutes longer).

In an embodiment, a method of cosmetic skin treatment using a magnetic field can include using a device as described herein for its intended purpose. For example, the device can be positioned near (e.g., within 1-10 mm) from a subject (e.g., a human patient) and turned on for a period of time.

In another embodiment, a method of fabricating a device as described herein can include providing each of the parts and assembling them to give the device.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

A device as shown in FIG. 1 was fabricated. The stimulation head included the four micro-coils shown in FIG. 2, and the device had the dimensions depicted in FIGS. 3 and 4. The circuit shown in FIG. 7 was housed in the case for driving the micro-coils, along with a 9 V lithium ion rechargeable battery. The power port shown in FIG. 1 was constructed as a mini-USB connector that could be used to charge the battery. The indicator light was an LED indicator configured to be green when stimulation is being provided and red when the battery was below 8.1 V. The circuit housed within the case had the values shown in FIG. 7 for the various components and was configured to provide a main frequency of 15 Hz and a sub-frequency of 4.386 kHz, with periods and pulses as depicted in FIGS. 5, 6, and 9. A sensor circuit, as shown in FIG. 8, and with the values for the components as shown in FIG. 8, was also included in the case.

Example 2

Figure 10A:
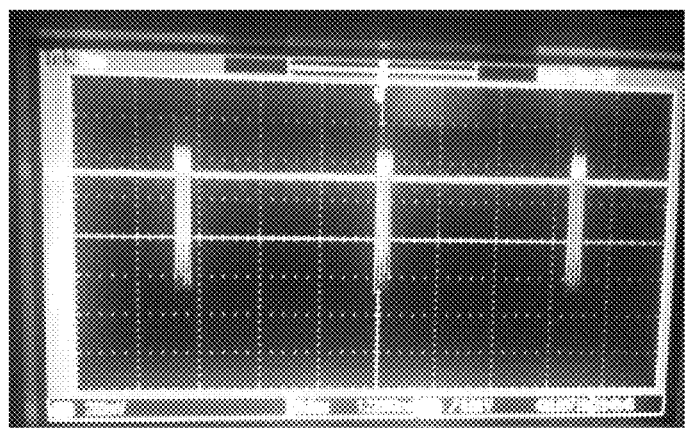
FIG. 10A is an image of real-time acquisition of a set of sub-pulses and main pulses that are output by a device according to an embodiment of the subject invention.
Figure 10B:
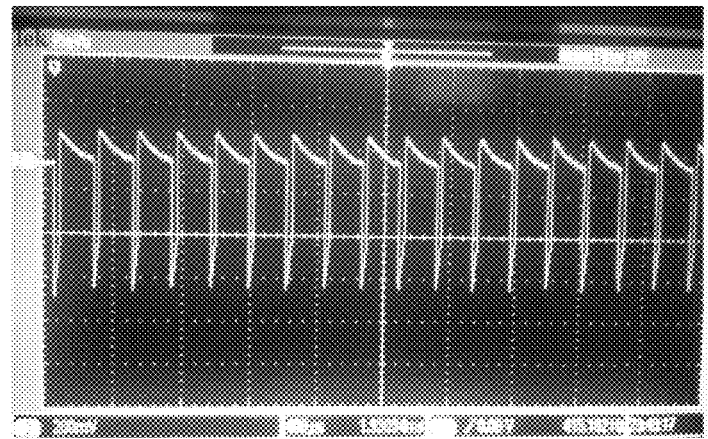
FIG. 10B shows an image of real-time acquisition of a set of sub-pulses.

The device of Example 1 was tested. The corresponding peak amplitude and waveform were detected using a standard coil probe (50 turns, 0.5 cm internal coil diameter, and 0.2 mm (#32) copper diameter). The signals were displayed using a digital oscilloscope (Tectronic MS 2024 mixed signal oscilloscope with 16 Ch. and 200 Mhz 16 s/s), and the results are shown in FIGS. 10A and 10B. FIG. 10A shows an image of real-time acquisition of a set of sub-pulses and main pulses that were output, and FIG. 10B shows an image of real-time acquisition of a set of sub-pulses only.

The magnetic field produced in the stimulation coils L1-L4 was sensed uninterruptedly during the stimulation session by sensory coil L5 (having a 0.5 cm internal diameter and 20 turns of 0.22 mm copper wire) (see also FIG. 8). In the sensor, the amplified signal in Q2 triggered the monostable Ne555 that activated the green LED 3, serving as an indicator of the magnetic field activity in stimulation coils L1-L4.

The peak intensity of the magnetic field was calculated using a Gaussmeter (model GM-2 Alpkalab Inc) with a hall probe. Each coil generated a magnetic field of roughly 1 milliTesla (10 Gauss) at a distance of 1 mm and approximately 20 mA of current flows through each coil. Glass slides of 1 mm were used to measure the decay of the intensity of the magnetic field with respect to distance using the stimulation device. The thickness of the surface was gradually increased to measure the decay of the magnetic field. Table 1 shows the magnetic field versus distance for five trials.

Figure 11:
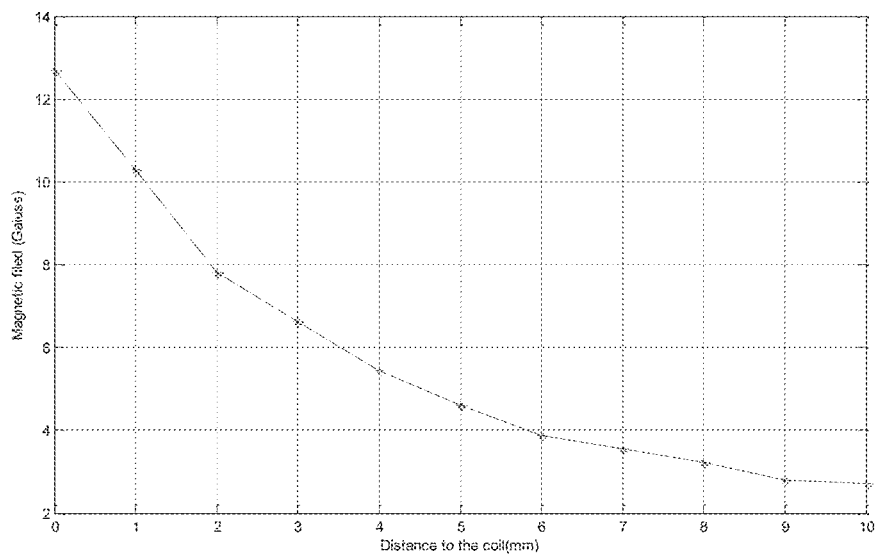
FIG. 11 shows a plot of magnetic field strength as a function of distance as output by an embodiment of the present invention.

FIG. 11 shows a plot of the average magnetic field (Gauss) as a function of distance from the coil(s) (mm). Referring to Table 1 and FIG. 11, there is a decay of the magnetic field as the device is moved farther away. The highest intensity is achieved close to the coil(s).

The skin's top layer is the epidermis, with a thickness of 0.05 to 0.2 mm, depending on its location. Below this layer is the dermis, with a thickness of 0.5 to 2 mm. In order to trigger collagen production, the dermis must be reached. As shown in this example, a device of the subject invention can reach this area with a low but sufficient intensity to activate the cells underneath.

TABLE 1

Magnetic Field vs. Distance.

| Distance (mm) | G1 (Gauss) | G2 | G3 | G4 | G5 | Average |
|---|---|---|---|---|---|---|
| 0 | 13.3 | 11.6 | 11.4 | 13.9 | 13.2 | 12.68 |
| 1 | 10.2 | 10.8 | 9.8 | 10.4 | 10.3 | 10.3 |
| 2 | 8.4 | 7.7 | 7.2 | 7.6 | 8.1 | 7.8 |
| 3 | 6.9 | 6.4 | 6.4 | 6.8 | 6.6 | 6.62 |
| 4 | 5.7 | 5.0 | 5.5 | 5.4 | 5.6 | 5.44 |
| 5 | 4.4 | 4.8 | 4.5 | 4.1 | 5.2 | 4.6 |
| 6 | 4.1 | 3.8 | 3.9 | 4.0 | 3.6 | 3.88 |
| 7 | 3.3 | 3.8 | 3.8 | 3.5 | 3.4 | 3.56 |
| 8 | 3.0 | 3.3 | 3.6 | 3.3 | 3.0 | 3.24 |
| 9 | 3.0 | 2.8 | 2.7 | 2.8 | 2.7 | 2.8 |
| 10 | 2.7 | 2.6 | 2.8 | 2.7 | 2.8 | 2.72 |

Example 3

Figure 12A:
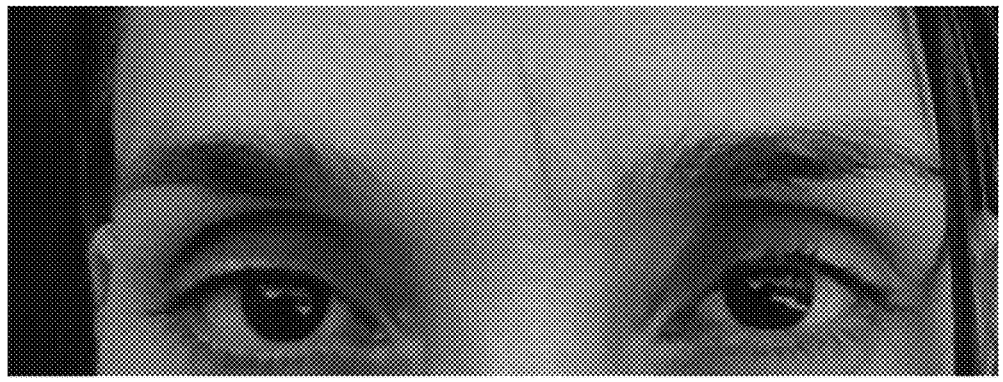
FIG. 12A shows an image of a test subject before treatment with a device according to an embodiment of the subject invention.
Figure 12B:
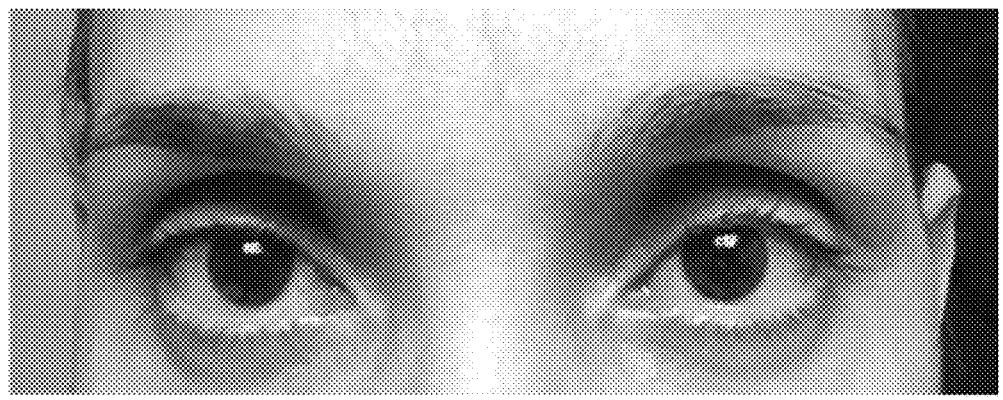
FIG. 12B is a picture of the test subject of FIG. 12A after treatment according to an embodiment of the subject invention.

The device of FIG. 1 was tested on a human subject. The device was used for two sessions/day, with a duration of 20 minutes/session, for 20 days of treatment on the subject shown in FIG. 12A. A session included positioning the device near the subject's face and turning it on for a period of 20 minutes, and then turning it off. FIG. 12B shows an image of the same portion of the subject's face after the treatment. Referring to FIGS. 12A and 12B, the device of the subject invention improves skin complexion and appearance, likely by increasing circulation and collagen and ATP production.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Bassett C A. 1993. Beneficial effects of electromagnetic fields. J Cell Biochem 51(4):387-393.
Agren M S, Engle M A, Mertz P M. 1994. Collagenase during burn wound healing: Influence of a hydrogel dressing and pulsed electrical stimulation. Plast Reconstr Surg 94:518-524.
Walker J L, Evans J M, Resing P, Guarnieri S, Meade P, Sisken B S. 1994. Enhancement of functional recovery following a crush lesion to the rat sciatic nerve by exposure to pulsed electromagnetic fields. Exp Neurol 125(2):302-305.
Ryaby J T. 1998. Clinical effects of electromagnetic and electric fields on fracture healing. Clin Orthop Relat Res 355Suppl:S205-S215.
Macias M Y, Battocletti J H, Sutton C H, Pintar F A, Maiman D J. 2000. Directed and enhanced neurite growth with pulsed electromagnetic field stimulation. Bioelectromagnetics 21(4):272-286.
Aaron R K, Ciombor D M, Simon B G. 2004. Treatment of nonunions with electric and electromagnetic fields. Clin Orthop Relat Res 419:21-29.
Bassett C A. 1993. Beneficial effects of electromagnetic fields. J Cell Biochem 51(4):387-393.
Patino O, Grana D, Bolgiani A, Prezzavento G, Mino J, Merlo A, Benaim F. 1996. Pulsed electromagnetic fields in experimental cutaneous wound healing in rats. J Burn Care Rehabil 17:528-531.
Bouzarjomehri F, Hajizadeh S, Sharafati A A, Firoozabadi S M P. 2000. Effects of Low frequency pulsed electromagnetic fields on wound healing in rat skin. Arch Intern Med 3:23-27.
Athanasiou A, Karkambounas S, Batistatou A, Lykoudis E, Katsaraki A, Kartsiouni T, Papalois A, Evangelou A. 2007. The effect of pulsed electromagnetic fields on secondary skin wound healing: An experimental study. Bioelectromagnetics 28(5):362-368.
Strauch B, Patel M K, Navarro J A, Berdichevsky M, Yu H L, Pilla A A. 2007. Pulsed magnetic fields accelerate cutaneous wound healing in rats. Plast Reconstr Surg 120(2):425-430.
Howard J D, Sarojini H, Wan R, Chien S. Rapid granulation tissue regeneration by intracellular ATP delivery—a comparison with Regranex. PLoS One, 2014 Mar. 17; 9(3): e91787. doi: 10.1371/journal.pone.0091787. eCollection 2014.

What is claimed is:
1. A handheld device for skin treatment, comprising:
a case;
a stimulation head coupled to the case and comprising at least one coil of conductive wire for generating a magnetic field; and
an electronic circuit, housed in the case, for driving the at least one coil to generate the magnetic field,
the electronic circuit being configured to drive the at least one coil to generate a main pulse of the magnetic field at a main frequency,
the main pulse comprising a plurality of sub-pulses at a sub-frequency that is greater than the main frequency, and
a magnetic field strength of the device, measured at a distance of 1 mm from the stimulation head, being from 5 Gauss to 15 Gauss.
2. The device according to claim 1, comprising a plurality of coils within the stimulation head.
3. The device according to claim 2, each coil having an outer diameter that is between 5.0 mm and 30.0 mm.
4. The device according to claim 1, a height of the stimulation head, measured in a direction perpendicular to an applicator surface of the stimulation head, being from 8.0 mm to 30.0 mm, a width of the stimulation head being from 6.0 mm to 40 mm, and a length of the stimulation head being from 40 mm to 120 mm.
5. The device according to claim 1, the main frequency being from 10-20 Hz and the sub-frequency is between 4.0 and 5.0 kHz.
6. The device according to claim 1, the main pulse having a duration that is less than an entire duration of a period of the main frequency, such that the period of the main frequency comprises the main pulse and a main rest period, and
each said sub-pulse having a duration that is less than an entire duration of a period of the sub-frequency, such that the period of the sub-frequency comprises the sub-pulse and a sub-rest-period.
7. The device according to claim 6, the main frequency being from 10-20 Hz and the sub-frequency is from 4 to 5 kHz.
8. The device according to claim 1, further comprising a rechargeable battery housed within the case, and a power port for charging the battery on an outer portion of the case.
9. The device according to claim 8, the battery being a lithium ion battery.
10. The device according to claim 9, the power port is being a mini USB connector.
11. The device according to claim 1, the stimulation head comprising polycarbonate, and sides of an outer surface of the case comprising rubber.
12. A method of providing magnetic stimulation to a human subject, comprising:
positioning the device according to claim 1 proximate to the subject; and
turning the device on to provide magnetic stimulation to the subject.
13. The method according to claim 12, the device being turned on and left proximate to the subject for a period of at least 20 minutes.
14. The method according to claim 13, the step of turning on the device that is proximate to the subject and leaving the device on for a period of time of at least 20 minutes being, performed at least twice a day for a plurality of days.
15. A handheld device for skin treatment, comprising:
a case;
a stimulation head coupled with the case and comprising a plurality of coils of conductive wire for generating a magnetic field, each said coil having an outer diameter that from 5 mm to 30 mm; and
an electronic circuit, housed in the case, for driving the coils to generate the magnetic field,
the electronic circuit being configured to drive the coils to generate a main pulse of the magnetic field at a main frequency,
the main pulse comprising a plurality of sub-pulses at a sub-frequency that is greater than the main frequency,
the main pulse having a duration that is less than an entire duration of a period of the main frequency, such that the period of the main frequency comprises the main pulse and a main rest period, each said sub-pulse having a duration that is less than an entire duration of a period of the sub-frequency, such that the period of the sub-frequency comprises the sub-pulse and a sub-rest-period, the main frequency being from 10.0 to 20.0 Hz and the sub-frequency is from 4.0 to 5.0 kHz, the duration of the main pulse being 2.5 ms to 18 ms, the duration of each sub-pulse being from 20 μs to 36 μs, a magnetic field strength of the device, measured at a distance of 1 mm from the stimulation head, being from 8 Gauss to 12 Gauss, and the device further comprising a rechargeable battery housed within the case, and a power port for charging the battery on an outer portion of the case.

16. The device according to claim 15, the battery being a lithium ion battery, the power port being a mini USB connector, the stimulation head comprising polycarbonate, and sides of an outer surface of the case comprising rubber.

17. A method of providing magnetic stimulation to a human subject, comprising:

positioning the device according to claim 16 proximate to the subject; and turning the device on to provide magnetic stimulation to the subject.

18. A handheld device for skin treatment, comprising:

a case;

a stimulation head coupled to the case and comprising at least one coil of conductive wire for generating a magnetic field; and an electronic circuit, housed in the case, for driving the at least one coil to generate the magnetic field, the electronic circuit being configured to drive the at least one coil to generate a main pulse of the magnetic field at a main frequency, the main pulse comprising a plurality of sub-pulses at a sub-frequency that is greater than the main frequency, the main pulse having a duration that is less than an entire duration of a period of the main frequency, such that the period of the main frequency comprises the main pulse and a main rest period, each said sub-pulse having a duration that is less than an entire duration of a period of the sub-frequency, such that the period of the sub-frequency comprises the sub-pulse and a sub-rest-period, the main frequency being from 10-20 Hz and the sub-frequency is from 4 to 5 kHz, the duration of the main pulse being 2.5-18 ms, and the duration of each said sub-pulse being 20-36 μs.

\* \* \* \* \*